United States Patent [19]

Sakurai et al.

[11] Patent Number: 4,716,224

[45] Date of Patent: Dec. 29, 1987

[54] CROSSLINKED HYALURONIC ACID AND ITS USE

[75] Inventors: Katukiyo Sakurai; Yoshio Ueno; Takashi Okuyama, all of Higashiyamato, Japan

[73] Assignee: Seikagaku Kogyo Co. Ltd., Tokyo, Japan

[21] Appl. No.: 729,558

[22] Filed: May 2, 1985

[30] Foreign Application Priority Data

| May 4, 1984 | [JP] | Japan | 59-88440 |
| Jan. 17, 1985 | [JP] | Japan | 60-4908 |
| Jan. 22, 1985 | [JP] | Japan | 60-8512 |
| Jan. 29, 1985 | [JP] | Japan | 60-13595 |
| Mar. 15, 1985 | [JP] | Japan | 60-50357 |

[51] Int. Cl.$^4$ .................. A61K 7/00; A61K 31/725
[52] U.S. Cl. .................. 536/55.1; 514/54; 514/825; 514/844; 514/953; 514/954
[58] Field of Search .............. 536/55.1; 514/54, 825, 514/953, 954, 844

[56] References Cited

U.S. PATENT DOCUMENTS

| 3,829,412 | 8/1974 | Kunz | 536/120 |
| 4,098,859 | 7/1978 | Cummisford et al. | 536/1.1 |
| 4,470,975 | 9/1984 | Berger et al. | 514/54 |
| 4,532,267 | 7/1985 | Allan | 536/55.1 |

FOREIGN PATENT DOCUMENTS

| 0185208 | 11/1982 | Japan | 514/54 |
| 0084225 | 5/1985 | Japan | 514/54 |

OTHER PUBLICATIONS

"Crosslinked Gels of Hyaluronic Acid, Torvard C. Laurent et al., Acta Chemica Scandinavica, vol. 18 (1964), Part I, pp. 274–275.

*Primary Examiner*—Ronald W. Griffin
*Attorney, Agent, or Firm*—Frishauf, Holtz, Goodman & Woodward

[57] ABSTRACT

Crosslinked hyaluronic acid or salts thereof prepared by crosslinking hyaluronic acid or salts thereof with a polyfunctional epoxy compound wherein a crosslinking index or number is 5 or more per 1000 repeating disaccharides composed of glucronic acid in hyaluronic acid and N-acetylglucosamine, and having various medical and cosmetic uses.

11 Claims, 10 Drawing Figures

Viscosity in 1% physiological saline
(centipoires) (20°C, slide speed 1.0sec⁻¹)

CROSSLINKED HYALURONIC ACID AND ITS USE

BACKGROUND OF THE INVENTION

This invention relates to a crosslinked hyaluronic acid. More particularly, it is concerned with a crosslinked hyaluronic acid or a salt thereof, which is prepared by crosslinking hyaluronic acid (hereinafter referred to as "HA") or a salt thereof with a polyfunctional epoxy compound.

HA is widely distributed in connective tissues such as skin, vitreous body or hyaloid, umbilical cord, synovial fluid, rooster comb and so on, like acidic mucopolysaccharides such as chondroitin sulfuric acid, heparan sulfuric acid, keratosulfuric acid. Also, HA is present between cells as a complex with protein in tissue, forms a jelly matrix owing to it high water retention and can play an important role in a living body such as maintenance of cell morphology, or protection against attack by bacteria or external power, control of cellular metabolism, lubricating action in joints (K. Meyer, Physiol. Rev., 27, 335, 1947).

As explained above, HA may exert a different action from mucopolysaccharides having a high charging property, which is believed to be derived from a different factor from a simple highly negative charging property, i.e., a high viscoelasticity of HA molecule.

Hitherto, there has been attempted to develop the above-mentioned actions of HA itself, typically, to treat arthritides, to prevent tissue surface from damage by anterior segment surgery in ophthamological field and so on by administering an isolated, purified HA into a living body or a cell system. However, the HA as in a living body may form a complex with certain, special proteins, show a stable and strong stringiness and a high viscoelasticity and play a specific role, whereas the HA as isolated and purified does hardly exert stringiness and it was very difficult in the prior art to extract and purify a highly viscous HA. Moreover, HA is known to undergo enzymatic decomposition or non-enzymatic oxidation-reduction decomposition after being administered to a living body, especially diseased sites (W. Pigman, S. Pizvi and H. L. Holley, Arthritis Rheumatism, 4, 240, 1961) so that it would be difficult to maintain its original viscosity. Satisfactory results have not yet been obtained.

On the other hand, it has been suggested to crosslink dextran or agarose with a crosslinking agent as disclosed in Japanese Patent Published Application No. 1321/1972.

Under these circumstances, we have made earnest studies to obtain a crosslinked HA which shows resistance to enzymatic decomposition or non-enzymatic oxidation-reduction decomposition and, as a result, it has been found that the intended objects can be achieved by crosslinking HA or a salt thereof with a polyfunctional epoxy compound. Further, it has been found that the present crosslinked HA or salts thereof can also show resistance to hyaluronidase and keep various properties of HA itself and thus can have a wide variety of medical and cosmetic uses.

SUMMARY OF THE INVENTION

It is, accordingly, a primary object of this invention to provide a novel crosslinked HA or a salt thereof which can exert various useful properties.

Other object of this invention is to provide new uses of the present crosslinked HA medicines, typically, an arthritis treating agent, a vitreous body treating agent or a medical molded product or as skin cosmetics.

The crosslinked HA and salts thereof according to this invention is a crosslinked HA which is prepared by crosslinking HA or salts thereof with a polyfunctional epoxy compound and, especially, characterized in that a crosslinking index or number is 5 or more per 1000 repeating disaccharides composed of glucuronic acid and N-acetylglucosamine of HA (hereinafter sometimes referred to as repeating disaccharides of HA).

The HA which may be employed in this invention may be any of those originated from various, non-limiting materials such as umbilical cord, rooster comb, vitreous body and so on and may have usually a molecular weight of several thousands to several millions. For purification thereof, there may be mentioned methods as disclosed in Japanese Patent Published Applications No. 145594/1977, No. 67100/1979 and No. 74796/1980. Also, as the HA salts, there may be mentioned an alkali metal salt such as sodium or potassium salt and an alkaline earth metal salt such as calcium or magnesium salt.

As used herein, the term "polyfunctional epoxy compound" is meant to indicate the compound which has at least one epoxy group and, further, one or more functional groups suitable for crosslinking hyaluronic acid including epoxy groups.

As such compounds, there may be exemplified by a halomethyloxirane compound, a bisepoxy compound and the like. As the halomethyloxirane compound there may be mentioned, for example, epichlorohydrin, epibromohydrin, $\beta$-methylepichlorohydrin, $\beta$-methylepibromohydrin and the like. As the bisepoxy compound, there may be mentioned, for example, 1,2-bis(2,3-epoxypropoxy)ethane, 1,4-bis(2,3-epoxypropoxy)butane, 1,6-bis(2,3-epoxypropoxy)hexane and a diglycidyl ether of bisphenol A or bisphenol F.

The crosslinked HA of this invention may be synthesized, for instance, according to the following procedures: usually, HA having a molecular weight of several thousands to several millions or a salt thereof is dissolved in an aqueous solution of an alkali to a concentration of not less than 0.5%, preferably not less than 1.0% and then a water-soluble organic solvent is added so as to amount to not less than 30%, preferably not less than 50%, of a whole liquid volume.

An aqueous alkali solution has preferably a pH of 8-14, more preferably a pH of 12-14. As the alkali, there may be usually mentioned an alkali or alkaline earth metal hydroxide such as sodium hydroxide, potasisum hydroxide or caldium hydroxide; an alkali or alkaline earth metal carbonate such as sodium carbonate or potassium carbonate. As the water-soluble organic solvent, there may be mentioned, for example, methanol, ethanol, isopropanol, acetone or dioxane; it may be used alone or in combination therewith. Addition of such water-soluble organic solvent may achieve effective reaction proceeding and also prevent the HA from decomposition with an alkali or reduction of molecular weight.

Next, to the resulting solution may be added one or more of said polyfunctional epoxy compounds and the resultant mixture is subjected to reaction at 0°–100° C., preferably 10°–60° C., more preferably 20°–40° C. Reaction period of time may vary depending upon the reaction temperature and 24–48 hours may be preferred at around 20° C., while 2-3 hours may be suitable at around 40° C.

In this reaction, a crosslinking index of the resulting crosslinked HA or salt thereof may be controlled by varying the molar ratio of the HA or salt thereof to the polyfunctional epoxy compound.

In order to obtain the desired crosslinked HA wherein a crosslinking number is 5 or more per 1000 repeating disaccharides of HA, it is satisfactory to employ one or more moles of the polyfunctional epoxy compound per mole of repeating disaceharide of HA.

In the HA having a molecular weight of approximately one million, when 1-10 moles of the polyfunctional epoxy compound are employed to one mole of repeating disaccharide of HA, there could be prepared a crosslinked HA having water solubility and stringiness (hereinafter frequently referred to as "s-crosslinked HA"; on the other hand, when not less than 10 moles of the epoxy compound are employed, there could be prepared a crosslinked HA having water insolubility and gel form (hereinafter frequently referred to as "is-crosslinked HA". Also, if one may use the HA having a molecular weight of approximately two millions, similar results could be obtained with 2-6 moles or not less than 6 moles of the epoxy compound, respectively.

The crosslinked HA which may be employed in this invention may also be prepared according to the following alternative procedures: To an alkali solution of the HA or salt thereof is added said water-soluble organic solvent and the resulting sticky precipitate is separated and then said polyfunctional epoxy compound is added. Then, reaction may be conducted at a temperature of 50° C. or lower to accomplish very efficient reaction. To obtain said sticky precipitate, one may apply decantation, for example, to remove supernatant. Reaction temperature is usually 10°-50° C., most preferably 20°-40° C. The higher the reaction temperature, the shorter the reaction period should be. Generally, about 2 hours may be preferred at around 40° C., while 24-48 hours may be suitable at around 20° C.

Illustratively, the s-crosslinked HA has a higher viscosity as compared with the starting HA and may usually have a viscosity of 650-60000 centipoises (cp) in a 1% physiological saline solution (20° C., slide speed, 1 sec$^{-1}$) and a non-Newtonian index of 0.5-0.8 (See H. Kondo, "Kitasato Igaku", 10, 485, 1980).

In application of the present crosslinked HA to a variety of arthritides, the crosslinked HA is usually dissolved in physiological saline to such a sufficient viscosity to pass through an injection needle, namely not more than 50000 cp, preferably 5000-30000 cp (20° C., slide speed 1 sec$^{-1}$). The present arthritis treating agent can show a high safety and a high resistance to tissue enzymes such as hyaluronidase etc. and may be useful for treatment of various arthritides, e.g., arthritis deformans, chronic articular rheumatism and so on.

In application of the present crosslinked HA to vitreous body, the crosslinked HA is dissolved in physiological saline so as to obtain a similar viscosity to that for arthritides. Injection may be accomplished, for example, according to Scott method, injection under twin inverted image ophthalmologic scopic examination with silicone oil (J. D. Scott, Trans. Ophthalmol. Soc. U.K., 93, 417, 1973). The present vitreous body agent may be applied to patients without taking the prone position. The present agent may be useful for treatment of difficult retinal detachment to treat and restore, i.e., retinal ablation with proliferation retinopathy of vitreous body, retinal detachment with huge dehiscence, proliferation traction retinal detachment or dehiscence-originated retinal detachment with diabetic retinopathy.

In the present skin cosmetics, the crosslinked HA may be preferably incorporated into cosmetics at 0.01-3% based upon the total cosmetic composition.

The present cosmetics may be optionally blended with other cosmetic additives such as a water-soluble thickening agent, a surface active agent, an oil hymectant, an ultraviolet absorbing agent, an alcohol, a chelating agent, a pH adjusting agent, an aseptic agent, a pigment and a perfume.

As the water-soluble thickening agent, there may be mentioned, for example, a polyamino acid or a salt thereof; a polyacrylic acid or a salt thereof; pulurane; carboxymethylcellulose; xanthan gum and the like. Such water-soluble thickening agent may be usually employed alone or in admixture with the two or more and may be incorporated at 0.01-5% based upon the total cosmetic composition.

Also, the present skin cosmetics may be blended with allantoin or its derivative which may be employed as a dermatological disease treating agent or a raw material for cosmetic industry. In this instance, it may be preferably incorporated at 0.01-5%.

The present cosmetics can show excellent water retention and excellent resistance to enzymes.

The present cosmetics may be applied, for example, after shaving, chaps, cracks, chappy skin and so on in the form of cosmetics such as creams, e.g. a nutrient cream, a hand cream, a body cream, a massage cream; nutrient milky lotions; face packs; face lotions, as well as hair cosmatics.

In molding a medical molded product with the present molding material, the present molding material is placed into a desired die, dehydrated and then dried.

A molded product may be of any shape, preferably in the shape of a film. There is; no limitation to molding procedures and casting is preferable.

An aqueous solution or suspension of the present molding material may be coated over a polymer, i.g., polyethylene sheet or film or a support, e.g., glass or metal plate to a desired thickness by means of an applicator, dehydrated and dried and then peeled off from said sheet, film or support to produce a film molded product.

A medical molded product obtained from the present molding material when dipped in water or physiological saline may gradually absorb water and may be dissolved. In a living body, the dissolved product may be decomposed with enzymes and the like and, therefore, if a crosslinking index may be controlled, it could be present within a living body or skin only over a necessary period and dissolved away from tissues as diseased tissues will be healed.

The present crosslinked HA, when given or applied to a living body, does not show any foreign body reaction and, when applied as a medical molded product, can show very high safety.

DESCRIPTION OF PREFERRED EMBODIMENT

This invention will be more fully illustrated by way of the following, non-limiting examples.

EXAMPLE 1

(1) Synthesis of s-crosslinked HA

In 450 ml of a 0.2N sodium hydroxide solution were dissolved 10 g of HA sodium salt (a molecular weight, $7.3\times10^5$) with cooling and the resulting solution was filtered with a 0.45μ microfilter. To the filtrate were added 40 ml of a 10N sodium hydroxide solution and then 500 ml of ethanol and 6.0 ml of epichlorohydrin with stirring. The reaction was effected at 20° C. for 24 hours and then the reaction mixture was adjusted to pH 6.4 with acetic acid. By addition of 500 ml of ethanol, there was separated a white precipitate, which was then recovered by filtration, washed well with ethanol and dried under reduced pressure.

Yield: 8.9 g.

Crosslinking index per 1000 repeating disaccharides in HA: 8.5.

Viscosity in 1% physiological saline (20° C., slide speed 1.0 sec$^{-1}$): 11000 centipoises (cp).

Non-Newtonian index: 0.60.

Elementary analysis: (%) C: 42.0, H: 4.87%, N: 3.29, Na: 5.81.

(2) Gel chromatography for s-crosslinked HA

Figure 1:
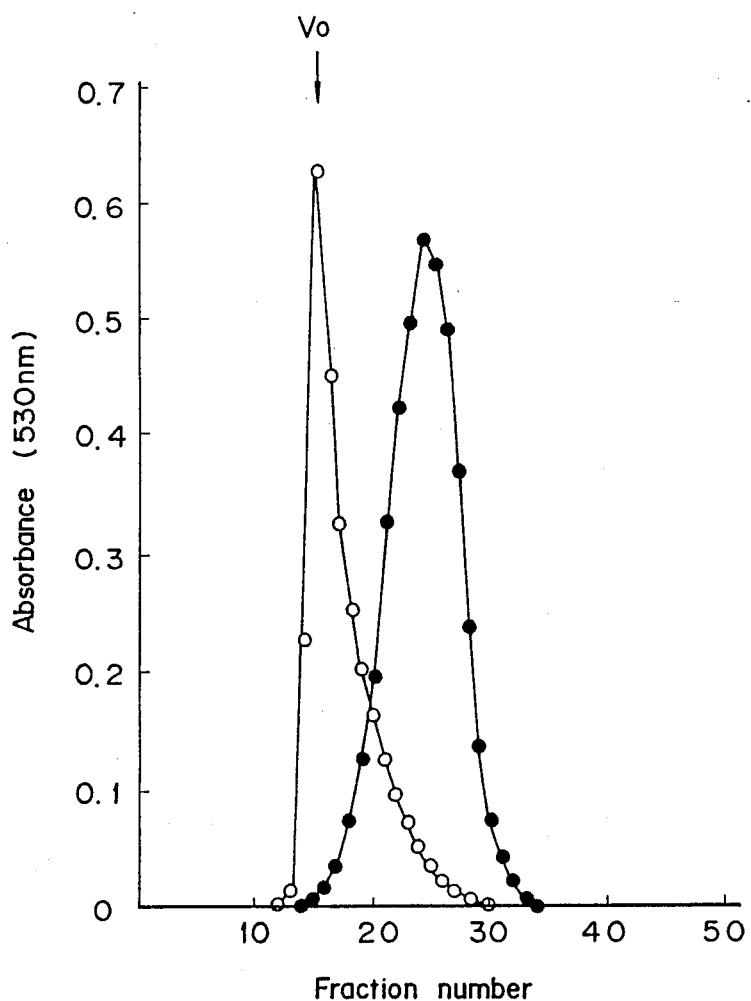

Using the s-crosslinked HA as synthesized in the above (1) and the HA used for synthesis in glass beads CPG 3000 (Electro Nucleonics. Inc.) column (6×850 mm), gel chromatography was effected. As a developing solvent, there was used a 1.5M sodium chloride solution in water adjusted to pH 8.5 with sodium hydroxide and each 0.52 ml of eluted fractions was separated and quantitatively determined according to the carbazole-sulfuric acid method. The results are shown in FIG. 1. In FIG. 1, the hollow circle "○" and full circle "●" show absorbance in each fraction of the s-crosslinked H and HA according to the carbazole-sulfuric acid method, respectively, and Vo represents the external volume of gel particle.

It is apparent from FIG. 1 that the present s-crosslinked HA is of a very high molecular weight, as compared with the HA.

(3) Non-Newton index of s-crosslinked HA

Figure 2:
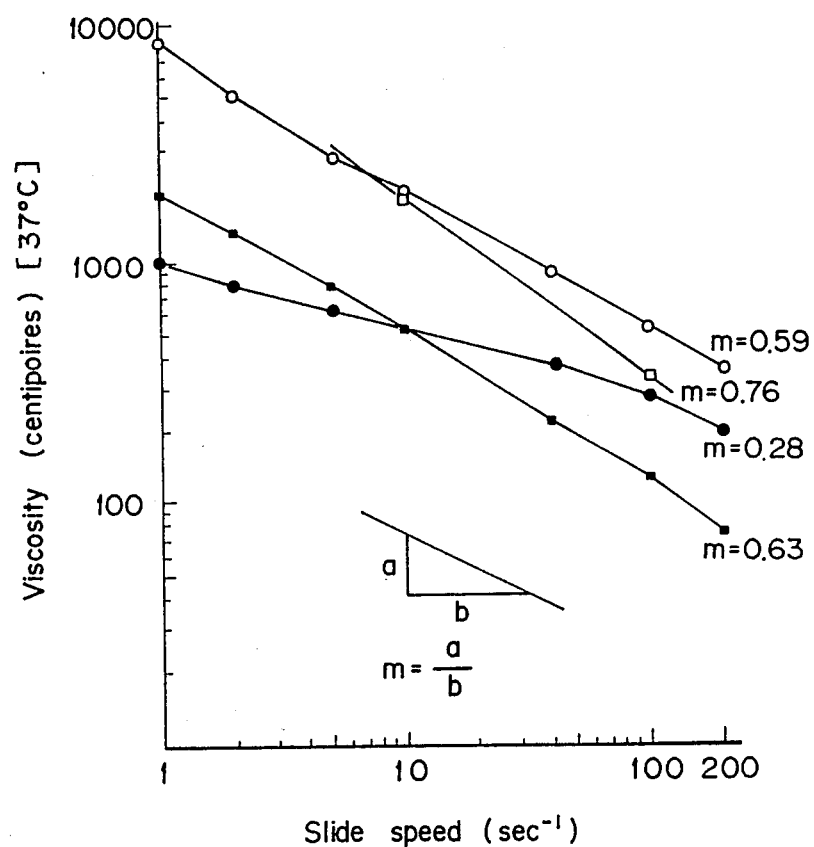

Using the s-crosslinked HA as synthesized in the above (1) and the HA used for synthesis in the form of a 1% physiological saline, viscosity was measured at 37° C. with varying shear rate by means of a rotary viscometer (a viscometer of type E manufactured by Tokyo Keiki Co., Ltd.) and the non-Newtonian index (m=a/b) was then calculated. Also, synovia of normal human and that of patient with arthritis deformans were similarly measured for viscosity and the non-Newton index was calculated. The results are shown in FIG. 2. In FIG. 2, the hollow circle (○), full circle (●), hollow square (□) and full square (■) show viscosities, respectively, 1% physiological saline solutions of the s-crosslinked HA and the HA as well as synovia of normal human and that of patient with light arthritis deformans at various slide speeds.

It is apparent from FIG. 2 that a 1% physiological saline solution of the present s-crosslined HA can show a very similar physical pattern to synovia of normal human.

(4) Stringiness of s-crosslinked HA

Figure 3:
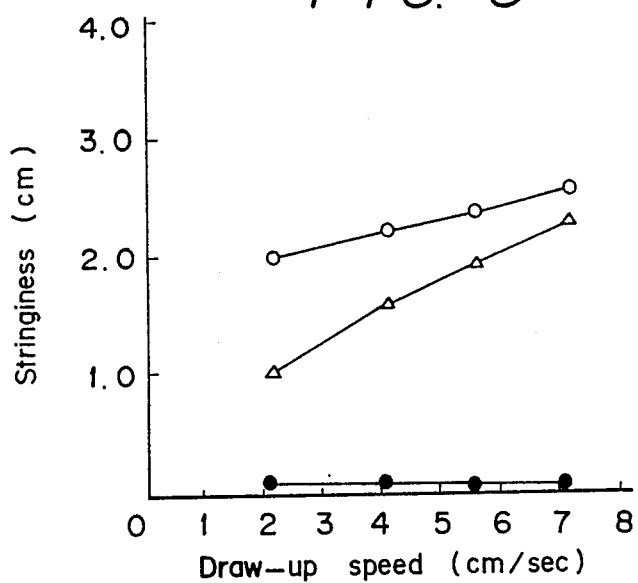

Stringiness of the s-crosslinked HA as synthesized in the above (1) and the HA used for synthesis was measured by means of an apparatus modeled after the Watanabe stringiness measurement apparatus (Hiroshi Ikeuchi, Journal of Orthopedic Surgery of Japan, 34, 175, 1960). The results are shown in FIG. 3. In FIG. 3, the hollow circle (○), hollow triangle (△) and full circle (●) show, respectively, stringiness of a 0.5% physiological saline solution of the s-crosslinked HA, and a 1% physiological saline solution of the same and a 1% physiological saline solution of the HA at respective draw-up speeds.

It is apparent from FIG. 3 that the present s-crosslinked HA has a high stringiness.

(5) Analgesic effect of s-crosslinked HA

The s-crosslinked HA as synthesized in the above (1) was tested for its analgesic effect as stated below.

Beagle dogs, irrespective of male and female, were given at the knee joint of either hind leg 20 μg or 2 mg of bradykinin or acetylcholine as a pain substance together with a physiological saline solution containing the s-crosslinked HA at 2.5 mg/0.5 ml and then changes in medicated hind leg loading were measured with lapse of time. Also, a physiological saline solution containing the HA sodium salt at 5 mg/0.5 ml such as used as a starting material in the above (1) was used as a control instead of the s-crosslinked HA solution. The analgesic effect was compared with 50% load recovery time at a normal time. The results are shown in Table 1.

TABLE 1

| Stimulant | 50% Recovery time (min.) |
|---|---|
| Bradykinin | 8.6 |
| Bradykinin + HA—Na | 3.4 |
| Bradykinin + S-crosslinked HA | 4.0 |
| Acetylcholine | 21 |
| Acetylcholine + HA—Na | 11 |
| Acetylcholine + S-crosslinked HA | 11 |

It is apparent from Table 1 that the present s-crosslinked HA shows a potent analgesic effect similarly to the HA sodium salt.

EXAMPLE 2

Synthesis of s-crosslinked HA

To 10 ml of a 1% aqueous solution of HA potassium salt (a molecular weight, $1.7\times10^6$) were added 0.1 ml of 10N potassium hydroxide and 5 ml of methanol and then 17 mg of epibromohydrin were added with stirring. Reaction was carried out at 20° C. for 24 hours. Then, the reaction mixture was adjusted to pH 6.5 with acetic acid and 10 ml of ethanol were added to produce a white precipitate. It was recovered by filtration and dried under reduced pressure.

Yield: 98 g.

Crosslinking index per 1000 repeating disaccharides in HA: 7.5.

Viscosity in 1% physiological saline (20° C., slide speed 1.0 sec$^{-1}$): 34000 (cp).

Non-Newtonian index: 0.65.

Elementary analysis: (%) C: 41.98, H: 4.79%, N: 3.30, K: 9.45.

EXAMPLE 3

Hyaluronidase resistance of s-crosslinked HA

Following the same procedures as in Example 1 (1) except that there was employed as a starting material HA sodium salt with a molecular weight of $7.3\times10^5$, there was synthesized the following three s-crosslinked HA.

(A)

Crosslinking index per 1000 repeating disaccharides in HA: 13.

Viscosity in 1% physiological saline (20° C., slide speed 1.0 sec$^{-1}$): 45500 (cp).

Non-Newtonian index: 0.77.

(B)

Crosslinking index per 1000 repeating disaccharides in HA: 11.5.
Viscosity in 1% physiological saline (20° C., slide speed 1.0 sec$^{-1}$): 28000 (cp).
Non-Newtonian index: 0.70.

(C)

Crosslinking index per 1000 repeating disaccharides in HA: 7.5.
Viscosity in 1% physiological saline (20° C., slide speed 1.0 sec$^{-1}$): 8000 (cp).
Non-Newtonian index: 0.61.

Viscosity of a 1% 0.1M acetic acid (pH 5.0) solution of said s-crosslinked HA or HA sodium salt used for synthesis was measured (20° C., slide speed 1.0 sec$^{-1}$) to give the following results;

| s-crosslinked HA (A) | 45000 cp |
| s-crosslinked HA (B) | 27000 cp |
| s-crosslinked HA (C) | 8000 cp |
| HA sodium salt | 1500 cp |

Figure 4:
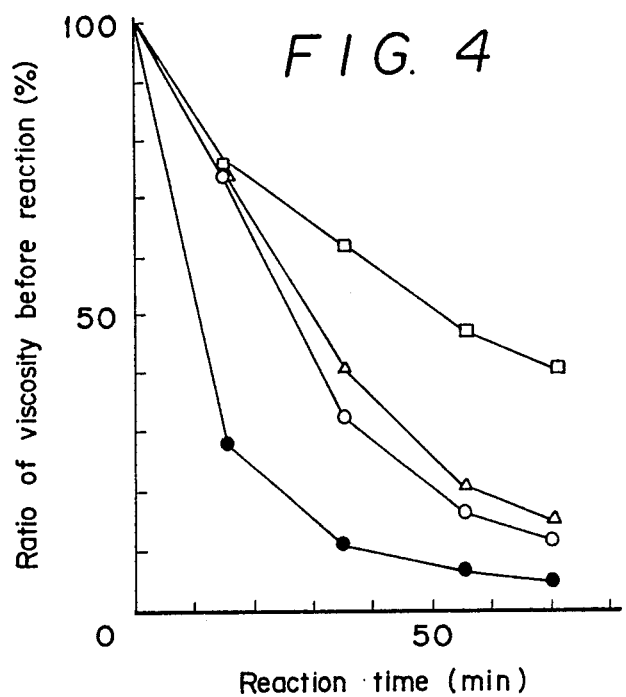

To the solution was added bovine testicles hyaluronidase at 0.09% by weight. Reaction was carried out at 50° C. and viscosity was measured after 15, 35, 55 and 70 minutes. Ratio to viscosity before reaction was calculated. The results are shown in FIG. 4. In FIG. 4, hollow square (□), hollow triangle (Δ), hollow circle (○), and full circle (●) represents ratios to viscosity before reaction at various reaction times in acetic acid solutions of s-crosslinked HA (A), (B) and (C) and HA sodium salt.

It is apparent from FIG. 4 that the present s-crosslinked HA has a higher resistance to hyaluronidase, as compared with HA and that the higher crosslinking index is, the higher the resistance is.

EXAMPLE 4

(1) Synthesis of is-crosslinked HA

In 500 ml of 1N sodium hydroxide were dissolved 10 g of HA sodium salt ( a molecular weight 7.3×10$^5$) under cooling and 500 ml of ethanol and 35 ml of epichlorohydrin were added. Reaction was carried out at 40° C. for 2 hours. 500 ml of water were added to the reaction mixture, which was then neutralized with acetic acid. The mixture was centrifuged at 3000 rpm and the precipitate was well washed with a 1.0M aqueous solution of sodium chloride. It was then washed with a 0.15M aqueous solution of sodium chloride, dehydrated with ethanol and dried.

Yield: 9.6 g.
Crosslinking index per 1000 repeating disaccharides in HA: 40.
Elementary analysis: (%) C: 41.66, H: 4.89%, N: 3.39, Na: 5.77.

(2) Affinity of is-crosslinked HA to collagen

The is-crosslinked HA as synthesized in the above (1) was weighed at 10.00, 5.56, 2.94, 2.00, 1.67 and 1.25 mg and suspended in 15 ml of 0.00167M acetic acid. To each of the suspensions was added and throughly admixed 1.0 ml of a 0.00167 acetic acid solution of 0.5% collagen (obtained and purified by dissolving bovine derma collagen with pepsin). The resulting mixture was stirred well for 10 minutes and then centrifuged at 3000 rpm. The precipitate was washed well with 0.00167M acetic acid, collagen was dissolved out with 2M-guanidine.hydrochloric acid (pH 7.0) and quantitatively determined according to Procop method. Also, according to Nagasawa et al method (Y. Inoue and K. Nagasawa, Carbohydr. Res., 111, 113, 1982), the HA wherein approximately 50% of carboxyl groups of uronic acid in HA were reduced with sodium borohydride (hereinafter referred to as "HA red") was crosslinked according to the above (1) to synthesize is-crosslinked HA red, which was also processed in the same manner as above. The results are shown in FIG. 5.

Figure 5:
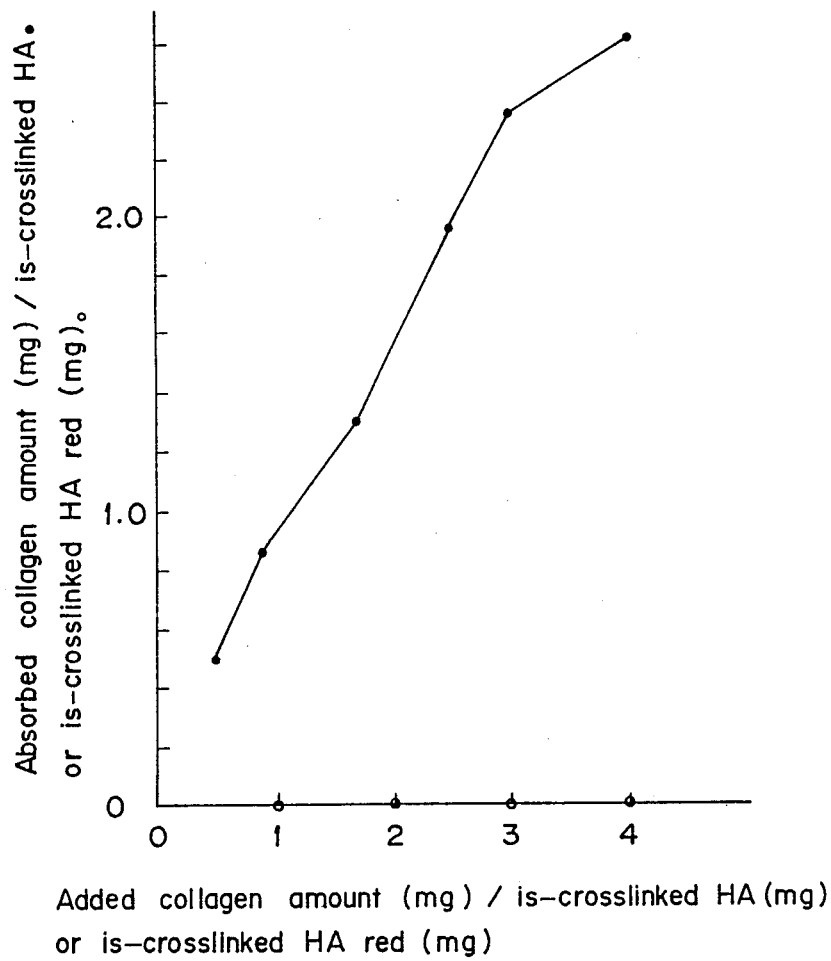

It is apparent from FIG. 5 that the present is-crosslinked HA shows an affinity to collagen.

(3) Affinity of is-crosslinked HA to proteoglycan

To a suspension of 500 mg of the is-crosslinked HA as synthesized in the above (1) in a 0.15M aqueous solution of sodium chloride were added 10 ml of a 0.1% solution of proteoglycan, which was prepared from bovine new born costal cartilage according to Rosenberg method (L. Rosenberg et al., J. Biol. Chem. 248, 3681, 1973), in a 0.15M aqueous solution of sodium chloride and the resulting mixture was stirred and then centrifuged at 3000 rpm. The precipitate was washed three times with 200 ml of a 0.15M aqueous solution of sodium chloride. Then, each stirring for 30 minutes and centrifugation at 3000 rpm was effected in turn with each 200 ml of a 0.5M aqueous solution of sodium chloride, 1.0M-guanidine.hydrochloric acid (pH 7.0), 2.0M-guanidine.hydrochloric acid (pH 7.0) and 5.0M-guanidine.hydrochloric acid. Each supernatant was quantitatively determined for uronic acid according to carbazole-sulfuric acid method to measure a proteoglycan amount. The results are shown in Table 2.

TABLE 2

| Fraction | Recovered amount of proteoglycan (recovery rate) |
|---|---|
| 0.15 M NaCl aqueous solution 1 | 0.572 mg (5.72%) |
| 0.15 M NaCl aqueous solution 2 | 0.080 mg (0.80%) |
| 0.15 M NaCl aqueous solution 3 | 0.010 mg (0.10%) |
| 0.15 M NaCl aqueous solution 4 | 0 |
| 0.5 M NaCl aqueous solution | 0.612 mg (6.12%) |
| 1.0 M guanidine.HCl | 2.004 mg (20.04%) |
| 2.0 M guanidine.HCl | 5.820 mg (58.20%) |
| 5.0 M guanidine.HCl | 0.745 mg (7.45%) |
| Total | 9.843 mg (98.43%) |

It is apparent from Table 2 that the present is-crosslinked HA shows an affinity to proteoglycan.

EXAMPLE 5

Synthesis of is-crosslinked HA

In 100 ml of 1.0N sodium hydroxide were dissolved 2.0 g of HA sodium salt (a molecular weight, 2.0×10$^6$) under cooling and 100 ml of dioxane and 4.3 g of 1,4-bis(2,3-epoxypropoxy)butane were added. Reaction was effected at 40° C. for 2 hours. To the reaction mixture were added 200 ml of water, the resultant mixture was neutralized with 1N hydrochloric acid and then centrifuged at 3000 rpm. The precipitate was washed well with a 1.0M aqueous solution of sodium chloride, and a 0.15M aqueous solution of sodium chloride, dehydrated with ethanol and then dried.

Yield: 1.7 g.
Crosslinking index per 1000 repeating disaccharides in HA: 13.
Elementary analysis: (%) C: 42.02, H: 4.87%, N: 3.29, Na: 5.88.

EXAMPLE 6

Crosslinking rate of crosslinked HA

In 5.0 ml of 1N sodium hydroxide was dissolved 100 mg of respective HA sodium salts having molecular weights of $3.7 \times 10^5$ and $7.3 \times 10^5$. To each solution were added 5 ml of ethanol and 25, 50, 100 and 200 µl of epichlorohydrin, respectively. Reaction was effected at 40° C. for 2 hours. After completion of the reaction, post-treatment was carried out in the same manner as in Example 1, (1).

Also, in 7.5 ml of 1N sodium hydroxide were dissolved 75 mg of HA sodium salt with a molecular weight of $1.7 \times 10^6$. To the solution were added 7.5 ml of ethanol and 40 µl or 80 µl of epichlorohydrin and reaction was effected at 40° C. for 2 hours.

Further, reaction was carried out with [2-$^{14}$C] epichlorohydrin (available from Amasham Japan Co., Ltd.) under the same reaction condition as above. Crosslinking rate was calculated based upon the radioactivity of this labelled compound. A relationship of crosslinking rate and viscosity is shown in Table 3.

It is apparent from Table 3 that crosslinking rate is proportional to viscosity.

TABLE 3

| Starting HA (molecular weight) | Epichlorohydrin (mol) HA (mol) | Crosslinking index per repeating 1000 disaccharides in | Viscosity in 1.0% physiological saline solution [20° C., slide speed 1.0 sec$^{-1}$] (cp) |
|---|---|---|---|
| $3.7 \times 10^5$ | 0 | 0 | 630 |
| | 1.28 | 6.3 | 630 |
| | 2.56 | 11.6 | 650 |
| | 5.12 | 20.9 | 2060 |
| | 10.2 | — | 15100 |
| $7.3 \times 10^5$ | 0 | 0 | 1500 |
| | 1.28 | 5.5 | 1650 |
| | 2.56 | 8.2 | 9240 |
| | 5.12 | 17.9 | 34300 |
| | 10.2 | 16.3 | 50000* |
| $1.7 \times 10^6$ | 0 | 0 | 11500 |
| | 2.68 | 5.6 | 20100 |
| | 5.37 | 11.8 | 55400* |

*Gelled if beyond this limit (insolubilized in water)

EXAMPLE 7

Acute toxicity

Male ddY strain mice of 4 weeks of age were preliminarily fed over 1 week. At the beginning of test, the body weight of mice was 21–27 g.

Mice were divided into groups, each group consisting of 15 animals. To each group was intraperitaneally administered the s-crosslinked HA of Example 1 in the form of a 0.5% physiological saline solution thereof at 1 ml/10 g of body weight (500 mg/kg), a 1% physiological saline solution thereof at 1 ml/10 g of body weight (1000 mg/kg) or a physiological saline solution at 1 ml/10 g of body weight.

Following the Irwin method, general manifestations were observed at the same time every day. After 7 days from administration, 5 animals of each group were sacrificed and, after 14 days, the remaining surviving animals were sacrificed. Administered sites and main organs were visually observed. The results are shown as seen below.

(i) No dead animals were observed in each group.
(ii) There were no difference in the groups administered at 500 mg/kg, those administered at 1000 mg/kg and control groups with regard to general manifestations, changes in body weight, uptake, water intake.
(iii) There was no difference between the groups administered at 500 mg/kg and control groups at autopsy on the 7th day or the 14th day, while there was more uronic acid in intraperitoneal remaining liquid in the groups administered at 1000 mg/kg on both the 7th and 14th days than that in control groups. It was estimated that the crosslinked HA was left at 3.6–3.8 mg/ml on the 14th day.
(iv) Influence upon organs was hardly observed in every group.

EXAMPLE 8

12 rabbits (an average body weight of 3 kg) were subcutaneously sensitized three times at ten days intervals with a mixture of 0.5 ml of a physiological saline solution of egg white albumin (10 mg/ml) with 0.5 ml of a physiological saline solution of Freund's complete adjuvant (10 mg/ml). On the ninth day from final sensitization, allergic arthritis was provoked by administering 0.2 ml of a physiological saline solution of egg white albumin (5 mg/ml) as an antigen into cavity of knee joint. Then, 0.1 ml of a physiological saline solution of s-crosslinked HA (20 mg/ml) was administered into cavity of knee joint together with 0.1 ml of a physiological saline solution of egg white albumin (10 mg/ml). After 3, 7 and 14 days from administration, the number of leaked calls within the cavity of the joint was measured. The results are shown in Table 4.

TABLE 4

| Days after administration of s-crosslinked HA | Number of leaked cells (× 10$^{-6}$ cell/joint) | | | |
|---|---|---|---|---|
| | Control group | | Group given with crosslinked HA | |
| | No. of animals | No. of cells | No. of animals | No. of cells |
| 3 | 2 | 25.1 | 2 | 11.8 |
| 7 | 2 | 6.8 | 2 | 3.5 |
| 14 | 2 | 3.0 | 2 | 1.5 |

It was apparent from Table 4 that the number of leaked cells in clearly reduced by administering the crosslinked HA.

EXAMPLE 9

Replacement of viteous body by crosslinked HA and measurement of restoration rate The following experiment was carried out by using a 1% physiological saline solution of the s-crosslinked HA.

In 10 rabbits (an average body weight of 3 kg) wherein experimental retinal ablation was brought about by drawing cortical vitreous body or hyaloid with a pincette (an ophthamologic forceps), there was made an exit hole in the sclera of the right eye to remove fluid under the retina, while there was made one incision in the flat part of corpus ciliare. Under examination by twin ophthalmologic scope, s-crosslinked HA was slowly injected by injecting a crosslinked HA injection needle behind lens. When the retina was restored with removal of fluid under the retina, injection needle and exit needle were drawn off. Removal and injection were repeated mutually through opposite holes so that the cavity in the vitreous body was replaced with the crosslinked HA as far as possible. After 10 days, the restored state was observed by means of a funduscopic camera. As a result, retinal ablation was obserned to be completely recovered in 7 rabbits (restoration rate, 70%).

EXAMPLE 10

Wound healing effect of crosslinked HA

Male Wistar-strain rats with 4 weeks of age were used for the following experiment, each group consisting of 6 animals.

Animals were hair-cut with electric hair clippers and then intramuscularly injected with pentobarbital sodium. Skin in the back was incised to about 2 cm at right and left parts and incised portions were immediately sewn by means of Michel sewing apparatus. After sewing, a 0.1% physiological saline solution of the s-crosslinked HA, a 0.2% physiological saline solution of allantoin or a mixture of said s-crosslinked HA solution and said allantoin solution in equal volume was coated over the left part with 0.1 ml once a day over 2 weeks. As a control, physiological saline was coated over the right part. After 2 weeks, the rats were sacrificed, sewing needles were removed and skin strip was prepared with a length of 2 cm, which each 1 cm was cut right and left at the center of said incision part, and a section of 1 cm. Tensile resistance of skin strip was measured by means of Tensitoron all-purpose tester RTM-50 (available from Toyo-Baldwin K. K.). Wound healing effect was determined from ratios to control. The results are shown in Table 5.

TABLE 5

| Sample | Wound healing effect |
| --- | --- |
| Crosslinked HA solution | 1.35 |
| Allantoin solution | 1.30 |
| Crosslinked HA solution plus allantoin solution | 1.44 |

EXAMPLE 11

(1) Preparation of cross-linked HA film

Using the s-crosslinked HA-1 in Example 1 and crosslinked HA as prepared in the same manner as in Example 1 except for varying amounts of epichlorohydrin, i.e., the following crosslinked HA-2, -3, -4 and -5, there were prepared films as seen below

| Crosslinked HA | Epichloro-hydrin (ml) | Viscosity in 1% physiological saline (20° C., slide speed 1.0 sec$^{-1}$) (cp) |
| --- | --- | --- |
| 1 | 2.4 | 3800 |
| 3 | 4.5 | 8000 |
| 4 | 7.5 | 30000 |
| 5 | 19.6 | Gel-like |

Each 1.5% aqueous solution of above HA was coated over a polyvinyl chloride plate to a certain thickness by means of an applicator and dehydrated by heating with a hot air at 40° C. for 20 hours. Each coated film was peeled off to form a film with a thickness of 0.003 cm. Also, a 1.5% aqueous solution of HA (a molecular weight, 800000) was treated in the same manner as above to form a HA film with a thickness of 0.003 cm as control.

Tensile resistance of the film was measured by means of Tensitron all-purpose tester RTM-50 (available from Toyo-Baldwin K. K.). The results are shown in Table 6.

TABLE 6

| Crosslinked HA film | Water content (%) | Tensile resistance (kg/cm) |
| --- | --- | --- |
| HA-1 | 10.2 | 1.67 |
| HA-2 | 12.4 | 1.60 |
| HA-3 | 11.3 | 1.65 |
| HA-4 | 14.6 | 2.20 |
| HA-5 | 12.8 | 1.57 |
| Control | 9.2 | 0.78 |

(2) Solubility test of film

To 5 mg of each film as prepared in the above (1) were added in a test tube 10 ml of physiological saline and the resulting mixture was allowed to stand for 30 minutes. Each test tube was vigorously shaken up and down 20 times and then allowed to stand for one day. Again, each test tube was vigorously shaken up and down 20 times and then centrifuged at 3000 rpm for 30 minutes. 0.1 ml of supernatant was recovered and determined for uronic acid according to the carbazole-sulfuric acid method to determine elution rate.

Figure 6:
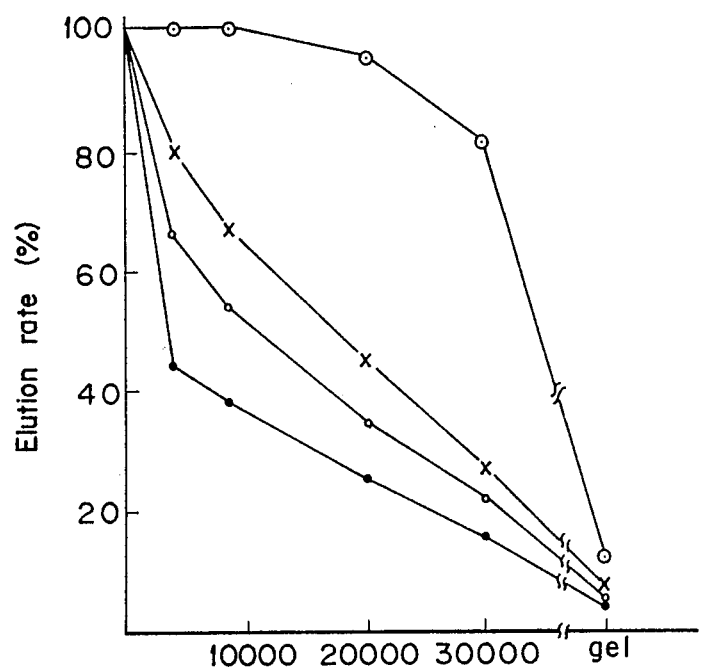

Once again, each test tube was vigorously shaken up and down 20 times and then allowed to stand for one day. Thereafter, the elution rate was determined in the same manner as above. The aforesaid procedures were repeated for 18 days. The results are shown in FIG. 6. In FIG. 6, full circle (●), hollow circle (○), X mark and dotted circle (◉) represent, respectively, elution rates after 1, 2, 3 and 18 days. The HA film was completely dissolved when allowed to stand at the first 30 minutes period.

It is apparent from FIG. 6 that solubility is reduced as viscosity or crosslinking index is increased.

(3) Storage of film by subcutaneously embedded test in guinea pigs

Each 7.6 mg of the crosslinked HA-1 film and HA film as in the above (1) was embedded into 10 male Hartley strain guinea pigs with 4 weeks of age (an average body weight of 250 g) under the skin of back incision part was sutured with nylon threads of 5–6 needles and then disinfected. After the 2nd, 5th, 10th and 20th days from transplantation, guinea pigs were killed with ether and then tissue with 3×4 cm was taken out from the under part of the subcutaneous layer of transplanted sites. The tissue thus taken was dipped and extracted into 40 ml of a 4M aqueous solution of guanidine at room temperature for 24 hours under stirring. As control, the tissue of the same part in non-treated guinea pigs was similarly treated.

By carbazole-sulfuric acid method, uronic acid was measured to determine residual rate. The results are shown in FIG. 7, wherein hollow circle (○) and full circle (●) represent, respectively, residual rates of crosslinked HA-1 film and HA film.

Figure 7:
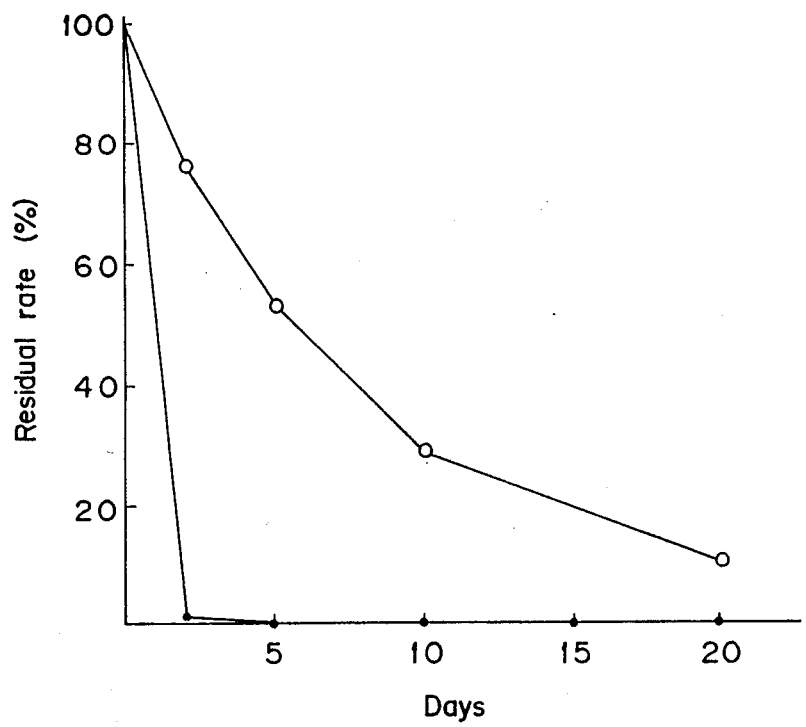

It is apparent from FIG. 7 that the present crosslinked HA-1 film can remain within tissues for a more prolonged period, as compared with the HA film.

Also, it can be seen from the results of the above (2) and (3) that the storage period of crosslinked HA in living body may be optionally controlled by controlling crosslinking index in crosslinked HA.

EXAMPLE 12

Figure 8:
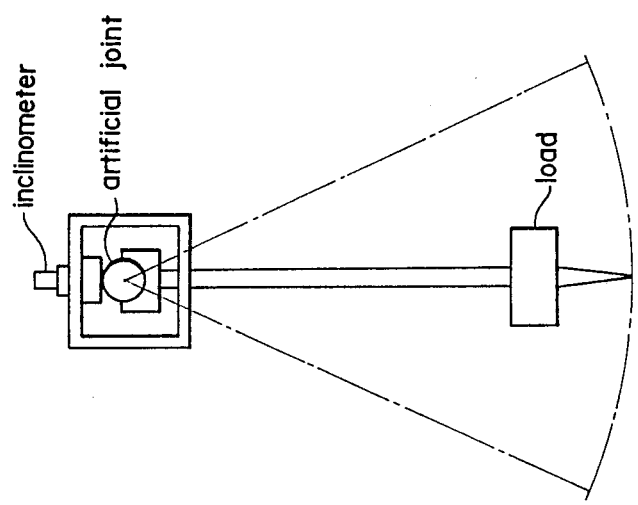

Measurement of fluid lubrication time by the swinging pendulum method using artificial hip joint The experimental apparatus provided with a pendulum as shown in FIG. 8 is to record electrical signals corresponding to inclinational angles of an artificial hip joint, which angles are measured by an inclinometer which is set right above the artificial hip joint supported on the central upper portion of the pendulum. Here, the inclinational angle is converted into the corresponding electrical signal. The artificial hip joint is composed of a ceramic sphere or ceramic porous ball.

By using the apparatus as shown in FIG. 8, the fluid lubrication time was measured with respect to HA having no stringiness, and normal human joint fluid and crosslinked HA-1 both having stringiness.

For HA, a sample having a molecular weight of $85 \times 10^4$ was used in physiological saline solutions having concentrations of 0.25, 0.5, 0.75, 1.5 and 2.0%, respectively.

Crosslinked HA-1 was used as a 0.5% solution in a physiological saline. For the normal human joint fluid, a sample having an HA concentration of 3.4 mg/ml was used.

A porous sphere was filled with a test liquid as the lubricating fluid, and the fluid lubrication time was measured by starting the free swinging with an intial amplitude of 5 rad immediately after loading with 2 kg and then recording the angle variation with the lapse of time as a swinging wave pattern.

Figure 9:
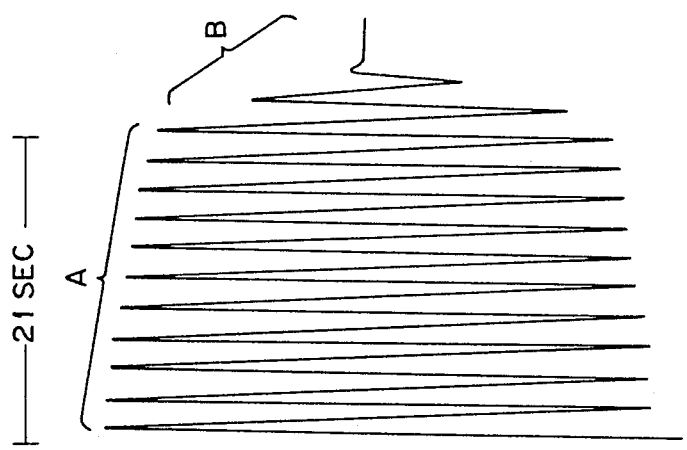

An example of the thus obtained wave pattern is shown in FIG. 9, in which the rigion A corresponds to fluid lubrication and the region B corresponds to boader line lubrication.

Figure 10:
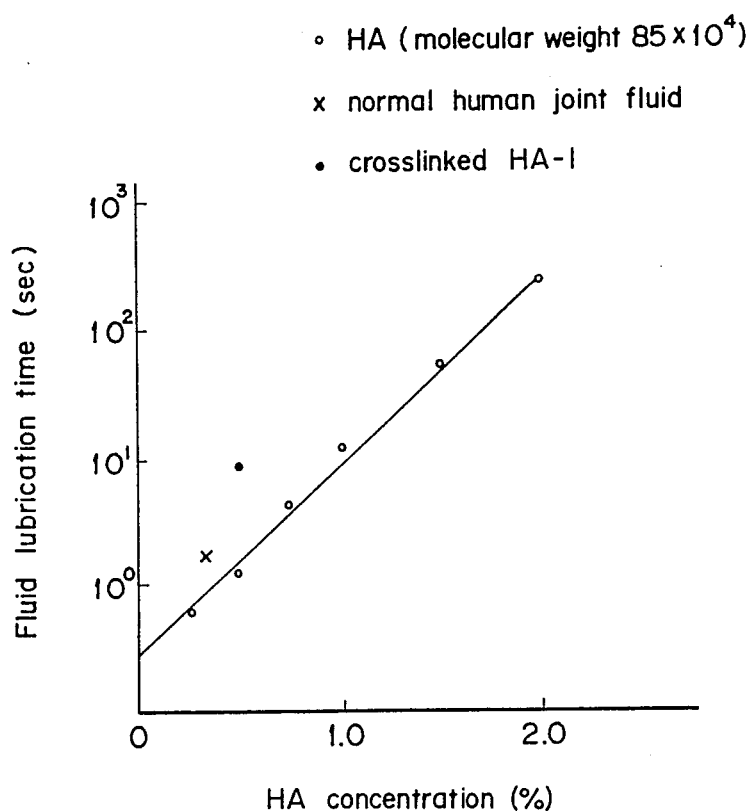

As a result, with respect to HA, it was found that the fluid lubrication time was extended in proportion to the HA concentration, as shown in FIG. 10, in which are shown also the fluid lubrication times for the normal hyman joint fluid and the crosslinked HA-1, respectively.

Therefore, it is considered that a crosslinked HA-1 having stringiness acts advantageously as a fluid lubricant which contributes to the lubrication mechanism of a joint.

EXAMPLE 13

Stringiness of normal human joint fluid (hereinafter referred to as NF.SF) and of osteoarthritis joint fluid (hereinafter referred to as OA.SF); restoration of stringiness by HA degradation of NF.SF with hyaluronidase The stringinesses of NF.SF and OA.SF were measured by adding HA (having a molecular weight of $7.3 \times 10^5$) and crosslinked HA-1 to NH.SF and OA.SF, respectively, so that the concentrations thereof might be 0.35%.

Further, NH.SF was treated by a hyarulonidase immobilized on a formylcellulofine (manufactured by Chissokogyo K.K., Japan), and to the thus obtained treated solution (hereinafter referred to as NF.SF deg HA) was added HA or crosslinked HA so that the conceantration thereof might be 0.35% to measure the stringiness thereof.

The results are shown in Table 7.

TABLE 7

|  | Stringiness (mm) |
|---|---|
| NH.SF (HA concentration 3.5 mg/ml) | 75 |
| OA.SF (HA concentration 1.3 mg/ml) | 40 |
| NH.SF + HA | 75 |
| NH.SF + crosslinked HA-1 | 75 |
| OA.SF + HA | 40 |
| OA.SF + crosslinked HA-1 | 60 |
| NH.SF deg HA | 0 |
| NH.SF deg HA + HA | 20 |
| NH.SF deg HA + crosslinked HA-1 | 45 |

The stringiness was measured by using a Watanabe type apparatus for measuring stringiness (see Ideuchi, Nippon Seikeigeka Zasshi 34, 175 (1962). The draw-up-speed was set to be 7 cm/sec.

From the analysis of NF.SF and OA.SF, it was found that NH.SF shows higher HA concentration, viscosity and stringiness as compared with OA.SF.

It is not absolutely clear how the stringiness acts on a joint, but it can be supposed that the stringiness plays a great roll on the joint lubricity. If the HA in NH.SF is degraded, the stringiness of the NH.SF is lost, and when a higher molecular weight HA or crosslinked HA-1 is added to the resulting NH.SF, the lost stringiness can be recovered to some extent. In such a case, crosslinked HA is more effective than HA. Therefore, it may be considered that NH.SF is composed of a high molecular weight HA bonded to a certain kind of protein through thier affinity, thereby showing the stringiness.

On the other hand, it may be considered that OA.SF shows small stringiness due to the HA having its molecular weight reduced, or being deffinient, or to the deffiency of a protein or proteins to be bonded with HA. Therefore, it can be understood that it is very effective to introduce a crosslinked HA having stringiness to a diseased joint.

We claim:

1. A crosslinked hyaluronic acid or a pharmaceutically acceptable salt thereof produced by crosslinking hyaluronic acid or a pharmaceutically acceptable salt thereof with a polyfunctional epoxy compound selected from the group consisting of halomethyloxirane compounds and a bisepoxy compound selected from the group consisting of 1,2-bis(2,3-epoxypropoxy) ethane, 1,4-bis(2,3-epoxypropoxy) butane, 1,6-bis(2,3-epoxypropoxy) hexane and a diglycidyl ether of biophenol A or bisphenol F, which has a crosslinking index of 5 to 20 per 1000 repeating disaccharide units composed of glucoronic acid and N-acetylglucosamine in hyaluronic acid, said crosslinked hyaluronic acid or pharmaceutically acceptable salt thereof being water soluble and stringy.

2. The crosslinked hyaluronic acid or a pharmaceutically acceptable salt thereof of claim 1, having a non-Newtonian index of 0.5 to 0.8.

3. The crosslinked hyaluronic acid or a pharmaceutically acceptable salt thereof of claim 2, wherein said polyfunctional epoxy compound is a halomethyloxirane compound.

4. The crosslinked hyaluronic acid or a pharmaceutically acceptable salt thereof of claim 3, wherein said halomethyloxirane compound is selected from the group consisting of epichlorohydrin, epibromohydrin, β-methylepichlorohydrin and β-methylepibromohydrin.

5. The pharmaceutically acceptable salts of claim 2, which is selected from the alkaline metal salts and the alkaline earth metal salts.

6. The crosslinked hyaluronic acid or pharmaceutically acceptable salt thereof of claim 1, which has a crosslinking index of 5 to less than 10.

7. A pharmaceutical composition for treating arthritides comprising as the active component, an effective amount of the crosslinked hyaluronic acid or a pharmaceutically acceptable salt thereof of claim 1, in combination with a pharmaceutically acceptable carrier or diluent.

8. An ophthanological composition for application to the eye comprising as the active component, an effective amount of the crosslinked hyaluronic acid or an opthanologically acceptable salt thereof of claim 1, in combination with an ophthanologically acceptable carrier or diluent.

9. A method of substituting vitreous humor into the eye of an animal comprising administering into the eye of said animal an effective amount of the composition of claim 8.

10. A cosmetic composition for applying to the skin comprising as the active component, an effective amount of the crosslinked hyaluronic acid or a cosmetically acceptable salt thereof of claim 1, in combination with a cosmetically acceptable carrier or diluent.

11. A molded medical film comprising a crosslinked hyaluronic acid or a pharmaceutically acceptable salt thereof of claim 1, in the form of a film.

* * * * *